United States Patent [19]

Clark et al.

[11] Patent Number: 4,904,653
[45] Date of Patent: Feb. 27, 1990

[54] THIENO[2,3-o]AZEPINE COMPOUNDS AND CNS AFFECTING USE THEREOF

[75] Inventors: Barry P. Clark, Lower Froyle; David E. Tupper, Reading, both of England

[73] Assignee: Lilly Industries Limited, Basingstoke, United Kingdom

[21] Appl. No.: 293,917

[22] Filed: Jan. 6, 1989

[30] Foreign Application Priority Data

Jan. 15, 1988 [GB] United Kingdom ............... 8800891

[51] Int. Cl.$^4$ ............ C07D 495/04; A61K 31/38
[52] U.S. Cl. ............................ 514/215; 540/594
[58] Field of Search ................... 540/594; 514/215

[56] References Cited

U.S. PATENT DOCUMENTS

| | | | |
|---|---|---|---|
| 4,414,225 | 11/1983 | Sauter et al. | 548/453 X |
| 4,575,504 | 3/1986 | Sauter et al. | 514/215 |
| 4,751,222 | 6/1988 | Brasstrup et al. | 514/213 |

OTHER PUBLICATIONS

A Barnett, *Drugs of the Future*, II, 49–56 (1986).
Andersen et al., *Eur. J. Pharmacol.*, 137, 291–92 (1987).
Aldrich Chemical Company, Inc., Catalog, Milwaukee, WI, 1988, p. 1430.
Reagents for Organic Synthesis, Louis F. Fieser and Mary Fieser, John Wiley and Sons, Inc., 1967, p. 314.

*Primary Examiner*—David B. Springer
*Attorney, Agent, or Firm*—Joseph A. Jones; Leroy Whitaker

[57] ABSTRACT

Compounds of the formula

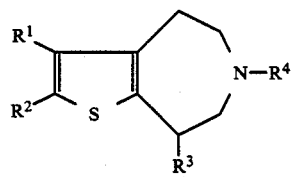

(I)

in which $R^1$ is hydrogen, hydroxy, nitro, cyano, halo, amino, acetamido, hydroxy-$C_{1-4}$ alkyl, carboxaldehydo, $C_{1-4}$ alkylcarbonyl, carboxy, $C_{1-4}$ alkoxy-carbonyl, $C_{1-4}$ alkyl, $C_{1-4}$ alkoxy, $C_{1-4}$ alkylthio, $C_{1-4}$ alkylsulphonyl or $C_{1-4}$ alkoxy-$C_{1-4}$ alkyl, $R^2$ is hydrogen, hydroxy, nitro, cyano, halo, amino, carboxamido, acetamido, hydroxy-$C_{1-4}$alkyl, carboxyaldehydo, $C_{1-4}$ alkylcarbonyl, carboxy, $C_{1-4}$ alkoxycarbonyl, $C_{1-4}$ alkyl, $C_{1-4}$ alkoxy, $C_{1-4}$ alkylthio, $C_{1-4}$ alkylsulphonyl, $C_{1-4}$ alkoxy-$C_{1-4}$ alkyl, oximino or aminomethyl, $R^3$ is optionally substituted phenyl or optionally substituted phenyl ortho condensed with an optionally substituted ring selected from benzene, cyclohexane, cyclohexene, cyclopentane or cyclopentene, in which ring one of the carbon atoms may be replaced by oxygen, sulphur or nitrogen, and $R^4$ is hydrogen, $C_{1-4}$ alkyl, $C_{2-4}$ alkenyl or optionally substituted benzyl; and salts thereof; have central nervous system activity.

8 Claims, No Drawings

THIENO[2,3-o]AZEPINE COMPOUNDS AND CNS AFFECTING USE THEREOF

This invention relates to chemical compounds and their use as pharmaceuticals.

The compounds of the invention have the formula

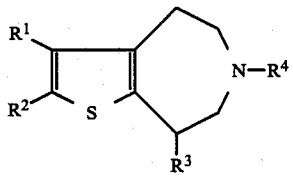

(I)

in which $R^1$ is hydrogen, hydroxy, nitro, cyano, halo, amino, acetamido, hydroxy-$C_{1-4}$ alkyl, carboxaldehydo, $C_{1-4}$ alkylcarbonyl, carboxy, $C_{1-4}$ alkoxy-carbonyl, $C_{1-4}$ alkyl, $C_{1-4}$ alkoxy, $C_{1-4}$ alkylthio, $C_{1-4}$ alkylsulphonyl or $C_{1-4}$ alkoxy-$C_{1-4}$ alkyl, $R^2$ is hydrogen, hydroxy, nitro, cyano, halo, amino, carboxamido, acetamido, hydroxy-$C_{1-4}$ alkyl, carboxaldehydo, $C_{1-4}$ alkylcarbonyl, carboxy, $C_{1-4}$ alkoxycarbonyl, $C_{1-4}$ alkyl, $C_{1-4}$ alkoxy, $C_{1-4}$ alkylthio, $C_{1-4}$ alkylsulphonyl, $C_{1-4}$ alkoxy-$C_{1-4}$ alkyl, oximino or aminomethyl, $R^3$ is optionally substituted phenyl or optionally substituted phenyl ortho condensed with an optionally substituted ring selected from benzene, cyclohexane, cyclohexene, cyclopentane or cyclopentene, in which ring one of the carbon atoms may be replaced by oxygen, sulphur or nitrogen, and $R^4$ is hydrogen, $C_{1-4}$ alkyl, $C_{2-4}$ alkenyl or optionally substituted benzyl; and salts thereof.

The compounds of the invention exhibit useful effects on the central nervous system.

When reference is made to halo, preferred groups are fluoro, chloro and bromo, and especially chloro and bromo. A $C_{1-4}$ alkyl group can be straight or branched and examples are methyl, ethyl, propyl, isopropyl or tert. butyl. Preferred alkyl groups are methyl and ethyl. A $C_{1-4}$ alkyl-carbonyl, $C_{1-4}$ alkoxy-carbonyl, $C_{1-4}$ alkoxy, $C_{1-4}$ alkylthio and $C_{1-4}$ alkylsulphonyl group are of the formula RCO—, ROCO—, RO—, RS— and $RSO_2$— respectively, where R is a $C_{1-4}$ alkyl group such as defined above. Preferred examples are acetyl, methoxycarbonyl, ethoxycarbonyl, methoxy, ethoxy, methylthio and ethylthio. The carboxaldehydo group is of the formula —CHO and the oximino group of the formula —CH=NOH. A hydroxy-$C_{1-4}$alkyl group is a $C_{1-4}$ alkyl group subsituted by —OH and includes for example hydroxymethyl and groups such as —CH(CH$_3$)OH and —C(CH$_3$)$_2$OH.

$R^1$ is preferably hydrogen, halo or $C_{1-4}$ alkythio, and $R^2$ is preferably hydrogen, hydroxy-$C_{1-4}$alkyl, halo or $C_{1-4}$ alkyl.

When $R^3$ is optionally substituted phenyl it can be phenyl or a phenyl group with one or more, such as one to three, substituents selected from for example nitro, cyano, amino, hydroxyl, trifluoromethyl, $C_{1-4}$ alkyl, especially methyl, $C_{1-4}$ alkoxy, especially methoxy and ethoxy, and halogen especially fluorine, chlorine or bromine. Preferred substituents are $C_{1-4}$ alkyl, $C_{1-4}$ alkoxy and halogen. When there is more than one substituent on the phenyl nucleus the substituents can of course be different. Alternatively, when $R^3$ is a condensed system, the phenyl group or condensed ring can be substituted with one or more substituents as defined above, and preferably with halogen, hydroxy or $C_{1-4}$ alkoxy. Values of $R^3$ when it is an ortho condensed system include naphthyl, benzofuranyl, dihydrobenzofuranyl, benzothienyl, chromanyl, chromenyl, indolyl, indolinyl, indanyl, indenyl, 1,2,3,4-tetrahydronaphthyl, dihydronaphthyl, and quinolinyl, each of which may be substituted with halogen, hydroxy or $C_{1-4}$ alkoxy, for example chlorochromanyl, methoxychromanyl, hydroxycromanyl and hydroxybenzofuranyl. Preferred examples are:

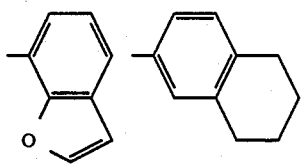

The most preferred value of $R^3$ is the unsubstituted phenyl nucleus.

When $R^4$ is $C_{2-4}$ alkenyl, it can be for example vinyl or allyl. $R^4$ is preferably $C_{1-4}$ alkyl and especially methyl. Optionally substituted benzyl includes benzyl and benzyl substituted on the phenyl nucleus with one or more, preferably one to three, substituents selected from for example nitro, cyano, amino, hydroxyl, trifluoromethyl, $C_{1-4}$ alkyl, especially methyl, $C_{1-4}$ alkoxy, especially methoxy and ethoxy, and halogen especially fluorine, chlorine or bromine. Preferred substituents are $C_{1-4}$ alkyl, $C_{1-4}$ alkoxy and halogen. When there is more than one substituent on the phenyl nucleus the substituents can of course be different.

A preferred group of compounds is of the formula (I) above, in which $R^1$ is halogen or $C_{1-4}$ alkylthio, $R^2$ is hydrogen, hydroxy-$C_{1-4}$alkyl, $C_{1-4}$alkyl or halo, $R^3$ is phenyl or benzofuranyl, and $R^4$ is hydrogen or $C_{1-4}$ alkyl.

The novel compounds are useful both in free amine form and as salts. For example the ring nitrogen atom is basic and furthermore there may be basic substituents on the molecule so the compounds can exist as acid addition salts. The acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric, salicyclic, o-acetoxybenzoic, nicotinic or isonicotinic acid, or organic sulphonic acids for example methane sulphonic, ethane sulphonic, 2-hydroxyethane sulphonic, toluene-p-sulphonic, or naphthalene-2-sulphonic acid.

In the case of compounds in which one or more of the substituents is acidic, for example, those bearing a carboxyl group, base addition salts can also be prepared. Examples of such salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, calcium hydroxide, methylamine, diethylamine, ethylene diamine, cyclohexylamine and ethanolamine. The potassium and sodium salt forms are particularly preferred.

In addition to pharmaceutically acceptable salts, other salts are also included in the invention such as, for example, those with picric or oxalic acids; they may serve as intermediates in the purification of the compounds or in the preparation of other, for example pharmaceutically acceptable, acid addition salts, or are useful for identification, characterisation or purification of the bases.

It will be appreciated that the compounds of formula (I) possess a chiral centre at the carbon atom of the nitrogen-containing ring to which the $R^3$ group is attached. All stereoisomers, and racemic mixtures, thereof are included within the scope of the invention. Isomers can be isolated from racemic mixtures by conventional methods such as by preparing suitable salts with a chiral acid and subsequently liberating the enantiomers or, alternatively, they can be prepared by methods devised to give the pure isomer.

The invention also includes a process for producing a compound of formula (I), which comprises cyclising a compound of the formula

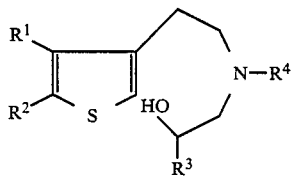

(II)

in which $R^1$, $R^2$, $R^3$, and $R^4$ have the above values, optionally followed when one or more of $R^1$, $R^2$ and $R^4$ is hydrogen by introduction of an appropriate substituent.

This cyclisation reaction is preferably carried out at a temperature of from 50° C. to 100° C. in the presence of an acid such as for example an alkane sulphonic acid, for instance methane sulphonic acid, and a trihaloacetic acid, for instance trifluoroacetic acid.

A preferred process is one which comprises cyclising a compound of formula (II) in which $R^1$ and $R^2$ are hydrogen, having the formula

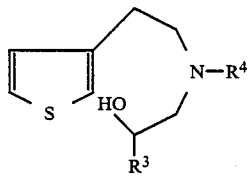

(III)

in which $R^4$ is hydrogen or $C_{1-4}$ alkyl and $R^3$ have the values given above, and reacting the product with an appropriate reagent to obtain the desired substituent values of $R^1$, $R^2$ and $R^4$.

Compounds of formula (II) can be prepared by reacting the appropriate amine of formula

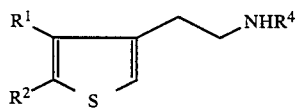

(IV)

with an oxirane of formula

(V)

The reaction is preferably performed at a temperature of from 50° C. to 100° C. in a polar organic solvent such as for example acetonitrile, dimethyl sulphoxide or dimethylformamide.

Compounds of formula (IV) are known or can be made by known procedures. The compounds of formula (IV) in which $R^1$, $R^2$ and $R^4$ are hydrogen can be readily prepared by reduction using lithium aluminium hydride and aluminium chloride of the appropriate cyanide of formula

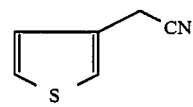

The resulting amine can be readily N-alkylated or N-alkenylated by standard procedures.

Preferred intermediates of formula (IV) in which $R^1$ is bromo and $R^2$ is hydrogen, can be prepared by the action of zinc and acetic acid on the tribromo compound of formula

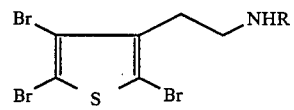

in which R is acyl, especially acetyl, or $R^4$. Such intermediates are in turn prepared by bromination of the corresponding unsubstituted compound.

Oxirane intermediates of formula (V) are known compounds or can be prepared by standard methods such as for example from the appropriate aldehyde by use of sodium hydride and trimethyl sulphoxonium iodide in dimethyl sulphoxide.

It will be appreciated that when $R^1$ and $R^2$ take values such as hydroxy or hydroxy-$C_{1-4}$alkyl it may be necessary prior to the cyclisation reaction to protect the group with a conventional protecting group which can subsequently be removed with ease to yield the desired compound, for example, by first preparing the $C_{1-4}$ alkoxy or $C_{1-4}$ alkoxy-$C_{1-4}$alkyl derivatives.

As mentioned above, it is often preferred to introduce the desired substituents after the cyclisation reaction. For example compounds in which $R^4$ is $C_{1-4}$ alkyl, $C_{2-4}$ alkenyl or optionally substituted benzyl can be prepared by simple and conventional alkylation techniques.

Compounds in which $R^1$ in formula (I) is halo can be prepared by the reaction of the appropriate compound in which $R^1$ is hydrogen and $R^2$ is already substituted, with a halogen in acetic acid. Compounds in which $R^1$ in formula (I) is halo and $R^2$ is hydrogen can be prepared by the reduction of the appropriate compound in which $R^2$ is bromo. A bromo group at the $R^1$ position can be replaced by other groups such as alkyl, alkylthio, chloro and nitrile using standard reaction conditions. A nitrile group at the $R^1$ position can be reduced to carboxaldehyde and hydroxymethyl groups.

Compounds in which $R^2$ in formula (I) is halo can be prepared by the reaction of the appropriate compound in which $R^2$ is hydrogen, with a halogen in acetic acid. A nitro group at this position can be introduced by reaction of nitric acid in acetic anhydride, and the nitro substituent converted by standard reduction and acylation to give an acetamido derivative from which the free amino compound can be liberated with acid treatment. Similarly a varied series of substituents can be introduced, starting with the preparation of the intermediates in which $R^2$ is carboxaldehydo.

As mentioned above, the compounds of the invention have useful central nervous system activity with low toxicity. This activity has been demonstrated in extensive testing using well-established procedures. More specifically the compounds have been shown to have activity in the $^3$H-SCH23390 binding test described by Billard et al., Life Sciences, Volume 35, pages 1885–1893, 1984. For example, compounds of the invention disclosed in the following Examples (with the exception of the compound of Example 1 which is an important intermediate in the preparation of other compounds of the invention) have an $IC_{50}$ value (the concentration of the compound required to reduce the binding of $^3$H-SCH23390 by 50%) of less than 5μM. This test indicates that the compounds interact with dopamine, $D_1$ receptors in the central nervous system and this is confirmed by their ability to alter the production of cyclic adenosine monophosphate by rat retinal homogenates (Riggs et al., J. Med. Chem., Volume 30, pages 1914–1918, 1987). The compounds of formula (I) and pharmaceutically-acceptable acid addition salts thereof, are potent centrally acting compounds which are useful in the treatment of depression, mild anxiety states, certain kinds of psychotic conditions such as schizophrenia and acute mania and parkinsonism.

The invention also includes a pharmaceutical composition comprising a pharmaceutically acceptable diluent or carrier in association with a compound of formula (I) in unprotected form; or a pharmaceutically acceptable salt thereof.

The compounds may be administered by various routes, for example by the oral or rectal route, topically or parenterally, for example by injection, and by inhalation, being usually employed in the form of a pharmaceutical composition. Such compositions are prepared in a manner well known in the pharmaceutical art and normally comprise at least one active compound. In making the compositions of the present invention, the active ingredient will usually be mixed with a carrier, or diluted by a carrier, and/or enclosed within a carrier which may, for example, be in the form of a capsule, sachet, paper or other container. When the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, aerosols (as a solid or in a liquid medium), ointments containing for example up to 10% by weight of the active compound, soft and hard gelatin capsules, suppositories, injection solutions and suspensions and sterile packaged powders. For administration by inhalation, particular forms of presentation include aerosols, atomisers and vaporisers.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl- hydroxybenzoate, talc, magnesium stearate and mineral oil. The compositions of the invention may, as is well known in the art, be formulated so as to provide quick, sustained or delayed release of the active ingredient after administration to the patient.

Where the compositions are formulated in unit dosage form, it is preferred that each unit dosage form contains from 5 mg to 500 mg, for example, from 25 mg to 200 mg. The term "unit dosage form" refers to physically discrete units suitable as unit dosages for human subjects and animals, each unit containing a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range of from 5 to 100 mg/kg. However, it will be understood that the amount administered will be determined by the physician in the light of the relevant circumstances including the condition to be treated, the choice of compound to be administered and the chosen route of administration, and therefore the above dosage ranges are not intended to limit the scope of the invention in any way.

The invention is illustrated by the following Examples. The structure of the compounds prepared was confirmed by nuclear magnetic resonance, infra-red, and mass spectra and the purity of the product was checked in most cases by HPLC. The reactions described give racemic mixtures.

EXAMPLE 1

(a) Thiophene-3-ethylamine

A solution of anhydrous aluminium chloride (26.6 g) in diethylether (100 ml) was added to a stirred suspension of lithium aluminium hydride (7.6 g) in ether (100 ml) under nitrogen atmosphere at room temperature. To the stirred mixture was added thiophene-3-acetonitrile (24.6 g) in ether dropwise over 30 minutes, the exothermic reaction causing the mixture to reflux.

After 1 hour water (8 ml) was added cautiously (exothermic) followed by 5M aqueous HCl (400 ml). The aqueous layer was separated and basified to pH~11 with 50% aqueous NaOH (160 ml). The aqueous solution was extracted with dichloromethane (2×200 ml) and the extracts dried over magnesium sulphate, filtered and evaporated to a pale yellow liquid. Distillation gave thiophene-3-ethylamine as a colourless liquid, b.p. 78°–79° at 6 mmHg.

(b) N-(2-hydroxy-2-phenylethyl) thiophene-3-ethylamine

A solution of thiophene-3-ethylamine (14.0 g), and styrene oxide (13.2 g) in acetonitrile (110 ml) was heated under reflux for 20 hours. The solution was cooled (freezer about −20°) to crystallise the title product as white needles.

A second crop of product was obtained by evaporation of the mother liquors, chromatography (silica, 1% MeOH in CH$_2$Cl$_2$ eluant), and recrystallisation from acetonitrile, m.p. 75° C.

(c)
8-Phenyl-5,6,7,8-tetrahydro-4-H-thieno[2,3-d]azepine hydrochloride

A solution of N-(2-hydroxy-2-phenylethyl)thiophene-3-ethylamine (12.6 g) and methane sulphonic acid (3.97 ml) in trifluoroacetic acid (60 ml) was heated under reflux for 2 hours. The reaction mixture was evaporated and the residue suspended in iced water (100 ml), basified with .880 ammonia solution (20 ml) to pH~10 and extracted with dichloromethane (2×100 ml). The extracts were dried, filtered and evaporated to a yellow viscous oil (12.2 g) of 8-phenyl-5,6,7,8-tetrahydro-4H-thieno[2,3-d]azepine.

The crystalline hydrochloride salt was prepared by addition of ethanolic hydrogen chloride (16.0 ml, 3.1M) to an ethanol solution of the product amine. The solution was cooled and diluted with ether to give 8-phenyl-5,6,7,8-tetrahydro-4H-thieno[2,3-d]azepine hydrochloride as an off-white powdery solid (m.p. 238°).

EXAMPLE 2

6-Methyl-8-phenyl-5,6,7,8-tetrahydro-4H-thieno[2,3-d]azepine

Method 1

A solution of 8-phenyl-5,6,7,8-tetrahydro-4H-thieno[2,3-d]azepine hydrochloride (4.0 g), formic acid (3.4 ml) and 40% formaldehyde (3.4 ml, 45 mmol) in dimethylformamide (14 ml) was heated to 100° for 1 hour. This mixture was evaporated and the residue dissolved in water (50 ml), basified with 0.880 ammonia solution to pH~10 and extracted with dichloromethane (2×50 ml). The extracts were dried filtered and evaporated to a viscous oil (4.63 g) which still contained residual dimethylformamide solvent.

Chromatography on silica, eluting with 5% methanol in dichloromethane, gave the title product as a viscous oil.

Method 2

N-(2-hydroxy-2-phenylethyl) N-methyl thiophene-3-ethylamine (prepared in Example 20 below) was cyclised by the method described in Example 1(c) and the title product isolated by chromatography.

EXAMPLE 3

2-Bromo-8-phenyl-5,6,7,8-tetrahydro-4H-thieno[2,3-d]azepine hydrochloride

A solution of bromine in acetic acid (1.03 ml, 10% v/v solution) was added dropwise to a stirred solution of 8-phenyl-5,6,7,8-tetrahydro-4H-thieno[2,3-d]azepine (0.53 g, 2 mmol, hydrochloride salt converted to free base by extraction between dichloromethane and aqueous ammonia) in acetic acid (5 ml) at room temperature. After 30 minutes the mixture was evaporated and the blue coloured solid residue recrystallised from ethanol (10 ml) to give 2-bromo-8-phenyl-5,6,7,8-tetrahydro-4H-thieno[2,3-d]azepine hydrobromide (m.p. 197°).

The hydrobromide salt was converted to the free base by extraction between aqueous ammonia and dichloromethane; then the hydrochloride salt (title product) was prepared in ethanol by adding ethanolic hydrogen chloride to give light green-blue crystals (m.p. 216°).

EXAMPLE 4

6-Methyl-2-nitro-8-phenyl-5,6,7,8-tetrahydro-4H-thieno[2,3-d]azepine hydrochloride A solution of concentrated nitric acid 70% (0.8 ml) in acetic acid (3 ml) was added dropwise to a stirred solution of 6-methyl-8-phenyl-4,6,7,8-tetrahydro-4H-thieno[2,3-d]azepine (1.11 g) in acetic anhydride (4 ml) and acetic acid (6 ml) cooled to 5°-10°.

After 24 hours at room temperature iced water (30 ml) was added, the mixture basified to pH~10 with 0.880 ammonia solution and extracted with dichloromethane (2×50 ml). The extracts were dried, filtered, and evaporated to a red oil (1.44 g). Ethanol (10 ml) and ethanolic hydrogen chloride were added to crystallise the title product (m.p. 154°).

EXAMPLE 5

2-Acetamido-6-methyl-8-phenyl-5,6,7,8-tetrahydro-4H-thieno[2,3-d]azepine

A suspension of 6-methyl-2-nitro-8-phenyl-5,6,7,8-tetrahydro-4H-thieno[2,3-d]azepine hydrochloride (0.20 g) and 10% palladium on carbon (20 mg) in acetic acid (18 ml), acetic anhydride (2 ml) was hydrogenated on a Parr apparatus for 24 hours at 70 psi. The mixture was filtered and the filtrate evaporated. The residue was dissolved in water (30 ml), basified to pH~11 with ammonia solution and extracted with dichloromethane (2×50 ml). The extracts were dried filtered and evaporated to a yellow viscous oil. Crystallisation from toluene gave the title product (m.p. 180°).

EXAMPLE 6

6-Methyl-8-phenyl-5,6,7,8-tetrahydro-4H-thieno[2,3-d]azepine-2-amine dihydrochloride A mixture of 2-acetamido-6-methyl-8-phenyl-5,6,7,8-tetrahydro-4H-thieno[2,3-d]azepine (10 mg) and 5M hydrochloric acid (2.0 ml) was heated to 90° for 30 minutes. The mixture was basified and extracted with dichloromethane (2×5 ml). The extracts were dried, filtered and evaporated to a yellow oil. This was immediately converted to the title product by dissolving in ethanolic hydrogen chloride and evaporating.

EXAMPLE 7

6-Methyl-8-phenyl-5,6,7,8-tetrahydro-4H-thieno[2,3-d]azepine-2-carboxaldehyde

Phosphorous oxychloride (4.6 ml) was added dropwise to a stirred solution of 6-methyl-8-phenyl-5,6,7,8-tetrahydro-4H-thieno[2,3-d]azepine (3.98 g) in dimethylformamide (17 ml) cooled in an ice bath. The mixture was heated to 60° for 18 hours and then evaporated. The residue was dissolved in iced water (50 ml), basified with 2M sodium hydroxide to pH~12 and extracted with dichloromethane (2×100 ml). The extracts were dried, filtered and evaporated to a brown oil. Crystallisation from hexane gave the title product as yellow crystals (m.p. 88°).

EXAMPLE 8

2-Hydroxymethyl-6-methyl-8-phenyl-5,6,7,8-tetrahydro-4H-thieno[2,3-d]azepine

A solution of sodium borohydride (0.73 g) in ethanol (30 ml) was added dropwise to a stirred solution of 6-methyl-8-phenyl-5,6,7,8-tetrahydro-4H-thieno[2,3-d]azepine-2-carboxaldehyde (1.50 g) in ethanol (30 ml)

cooled in an ice bath. After 30 minutes the solution was evaporated, the residue dissolved in water (100 ml) and extracted with dichloromethane (2×100 ml). The extracts were dried filtered and evaporated to a viscous oil. Crystallisation from cyclohexane (15 ml) gave the title product, m.p. 112°.

EXAMPLE 9

3-Bromo-2-hydroxymethyl-6-methyl-8-phenyl-5,6,7,8-tetrahydro-4H-thieno[2,3-d]azepine Bromine (0.23 ml) was added dropwise to a stirred solution of 2-hydroxymethyl-6-methyl-8-phenyl-5,6,7,8-tetrahydro-4H-thieno[2,3-d]azepine (1.20 g) and sodium acetate trihydrate (1.8 g) in acetic acid (60 ml) at room temperature. After 1 hour the solution was evaporated, the residue dissolved in water (100 ml), basified to pH~11 with 0.880 ammonia solution and extracted with dichloromethane (2×100 ml). The extracts were dried, filtered and evaporated to a brown oil (1.74 g). Chromatography on silica, eluting with 2% methanol in dichloromethane gave a solid (0.80 g) which was recrystallised from toluene (15 ml) to give the title product (m.p. 141°).

EXAMPLE 10

Z- and E-6-Methyl-8-phenyl-5,6,7,8-tetrahydro-4H-thieno[2,3-d]azepine-2-carboxaldoxime A solution of 5M sodium hydroxide (2.0 ml) was added to a stirred solution of 6-methyl-8-phenyl-5,6,7,8-tetrahydro-4H-thieno[2,3-d]azepine-2-carboxaldehyde (0.52 g) and hydroxylamine hydrochloride (0.20 g) in ethanol (10 ml) at room temperature. After 30 minutes the solution was evaporated. Water was added to the residue and extracted with dichloromethane (3×10 ml). The extracts were dried filtered and evaporated to a brown solid (0.49 g) which contained a mixture of the title products, 60:40 ratio E-:Z- isomers. The mixture was separated by fractional crystallisation. Recrystallisation from diethylether (40 ml) and then ethanol gave powdery crystals of the Z-product (m.p. 199°). The ether solution was reduced in volume to give a second crop and recrystallised from ethanol to give cubic crystals (m.p. 203°) of the E- product.

EXAMPLE 11

6-Methyl-8-phenyl-4,6,7,8-tetrahydro-4H-thieno[2,3-d]azepine-2-carbonitrile

Trifluoroacetic anhydride (0.114 ml) was added dropwise to a stirred solution of Z- and E-6-methyl-8-phenyl-5,6,7,8-4H-thieno[2,3-d]azepine-2-carboxaldoxime (0.20 g) and anhydrous pyridine (0.128 g) in dry tetrahydrofuran (5 ml) cooled to 0°–5°. After 4 hours at room temperature, water (20 ml) was added, basified with 0.880 ammonia solution and extracted with dichloromethane (2×20 ml). The extracts were dried, filtered and evaporated to a viscous oil. Chromatography on silica eluting with 4% methanol in dichloromethane gave the title product as an oil.

EXAMPLE 12

2-Chloro-6-methyl-8-phenyl-5,6,7,8-tetrahydro-4H-thieno[2,3-d]azepine hydrochloride Sulphuryl chloride (0.16 ml) was added to a stirred solution of 6-methyl-8-phenyl-5,6,7,8-tetrahydro-4H-thieno[2,3-d]azepine hydrochloride (0.49 g free base converted to hydrochloride salt with ethanolic hydrogen chloride) at room temperature. After 2 hours the mixture was evaporated and the solid residue recrystallised twice from ethanol (5 ml) to give the title product as white crystals (m.p. 198°).

EXAMPLE 13

2-Bromo-6-methyl-8-phenyl-5,6,7,8-tetrahydro-4H-thieno[2,3-d]azepine hydrochloride 2-Bromo-6-methyl-8-phenyl-5,6,7,8-tetrahydro-4H-thieno[2,3-d]azepine hydrochloride was prepared by bromination of 6-methyl-8-phenyl-5,6,7,8-tetrahydro-4H-thieno[2,3-d]azepine using the method described in Example 3, white crystals (m.p. 210°).

EXAMPLE 14

6-Methyl-2-methylthio-8-phenyl-5,6,7,8-tetrahydro-4H-thieno[2,3-d]azepine

A solution of n-butyl lithium in n-hexane (1.6M, 0.75 ml) was added dropwise to a stirred solution of 2-bromo-6-methyl-8-phenyl-5,6,7,8-tetrahydro-4H-thieno[2,3-d]azepine (0.40 g hydrobromide salt converted to free base by aqueous ammonia/dichloromethane extraction) in dry tetrahydrofuran (10 ml) cooled to −70° under nitrogen. After 10 minutes at −70° dimethyl disulphide (0.11 ml) was added dropwise and the mixture allowed to warm to room temperature. After 30 minutes the solution was evaporated, water (10 ml) added to the residue and extracted with dichloromethane (2×5 ml). The extracts were dried, filtered and evaporated to a pale yellow solid. Recrystallisation twice from n-hexane (4 ml) gave white needles (m.p. 90°) of the title product.

EXAMPLE 15

3-Bromo-6-methyl-2-methylthio-8-phenyl-5,6,7,8-tetrahydro-4H-thieno[2,3-d]azepine 3-Bromo-6-methyl-2-methylthio-8-phenyl-5,6,7,8-tetrahydro-4H-thieno[2,3-d]azepine was prepared from 6-methyl-2-methylthio-8-phenyl-5,6,7,8-tetrahydro-4H-thieno[2,3-d]azepine by the method described in Example 9 as an oil.

EXAMPLE 16

2,6-Dimethyl-8-phenyl-5,6,7,8-tetrahydro-4H-thieno[2,3-d]azepine

A solution of n-butyl lithium in n-hexane (1.6M 0.75 ml) was added dropwise to a stirred solution of 2-bromo-6-methyl-8-phenyl-5,6,7,8-tetrahydro-4H-thieno[2,3-d]azepine (1 mmol) in dry tetrahydrofuran (10 ml) cooled to −70° under nitrogen. After 10 minutes at −70° dimethyl sulphate (0.114 ml) was added dropwise and the mixture allowed to warm to room temperature. After 30 minutes water (20 ml) was added and extracted with dichloromethane (2×20 ml). The extracts were dried filtered and evaporated to a yellow oil (0.27 g). Chromatography on silica eluting with 4% methanol in dichloromethane gave an oil (0.19 g) which contained a 4:1 mixture of the title product:2-des methyl product. Further purification using reverse phase preparative high pressure liquid chromatography gave the pure title product as an oil.

EXAMPLE 17

3-Bromo-2,6-dimethyl-8-phenyl-5,6,7,8-tetrahydro-4H-thieno [2,3-d]azepine

3-Bromo-2,6-dimethyl-8-phenyl-5,6,7,8-tetrahydro-4H-thieno[2,3-d]azepine was prepared by bromination of 2,6-dimethyl-8-phenyl-5,6,7,8-tetrahydro-4H-thieno[2,3-d]azepine by the method described in Example 9 as an oil.

EXAMPLE 18

2,3-Dibromo-6-methyl-8-phenyl-5,6,7,8-tetrahydro-4H-thieno [2,3-d]azepine hydrochloride Bromine (0.31 ml) was added to a stirred solution of 2-bromo-6-methyl-8-phenyl-5,6,7,8-tetrahydro-4H-thieno[2,3-d]azepine (0.97 g) in acetic acid (50 ml) at room temperature. After 24 hours the dark mixture was evaporated, water (50 ml) added to the residue and extracted with dichloromethane (2×50 ml). The extracts were dried, filtered and evaporated. The residue was dissolved in ethanol and ethanolic hydrogen chloride, evaporated, and recrystallised from ethanol to give the title product (m.p. 228°).

EXAMPLE 19

3-Bromo-6-methyl-8-phenyl-5,6,7,8-tetrahydro-4H-thieno [2,3-d]azepine

Method 1

A solution of n-butyl lithium in hexane (0.2 ml) was added dropwise to a stirred solution of 2,3-dibromo-6-methyl-8-phenyl-5,6,7,8-tetrahydro-4H-thieno[2,3-d]azepine (0.10 g) in dry tetrahydrofuran (5 ml) at −70° under nitrogen. After 30 minutes at −70° water (1 ml) was added, the mixture allowed to warm to room temperature, diluted water (15 ml) and extracted with dichloromethane (2×15 ml). The extracts were dried, filtered, evaporated and the residue chromatographed on silica eluting with 2% methanol in dichloromethane to give the title product (m.p. 64°).

Method 2

Zinc dust (20 mg) was added portionwise to a stirred solution of 2,3-dibromo-6-methyl-8-phenyl-5,6,7,8-tetrahydro-4H-thieno[2,3-d]azepine (0.10 g) in acetic acid heated to ~80°. After 20 hours the mixture was filtered, the filtrate evaporated and the title product isolated by dichloromethane extraction.

Method 3

Bromine (3.39 ml) was added dropwise to a stirred solution of 6-methyl-8-phenyl-5,6,7,8-tetrahydro-4H-thieno[2,3-d]azepine (3.98 g) and sodium acetate trihydrate (12.5 g) in acetic acid (60 ml) at room temperate. The mixture was heated to 50° for 6 hours. Zinc dust (5.3 g) was added portionwise and the mixture heated under reflux for 18 hours. The reaction mixture was evaporated and the title product isolated by dichloromethane extraction and chromatography on silica.

Method 4

3-Bromo-8-phenyl-5,6,7,8-tetrahydro-4H-thieno[2,3-d]azepine hydrochloride prepared in Example 21 was N-methylated by the method described in Example 2, method 1 to give the title product.

EXAMPLE 20

(a) Methyl thiophene-3-ethylamine (i) Formic acid 98% (1.7 ml) was added to a solution of thiophene-3-ethylamine (5.0 g) in toluene (50 ml) and the mixture heated under Dean and Stark conditions for 1 hours. The solution was evaporated to a pale liquid (5.97 g) of 3-thienylethyl formamide.

(ii) A solution of 3-thienylethyl formamide (5.82 g) in dry diethylether (100 ml) was added to a stirred suspension of lithium aluminium hydride (1.71 g) in diethylether (30 ml) at room temperature under nitrogen. After 1½ hours at reflux temperature the mixture was allowed to cool and the following were added, water (1.8 ml), 2M sodium hydroxide (3.6 ml) and water (5.4 ml). After vigorous stirring for 30 minutes the suspension was filtered and the filtrate evaporated and distilled to give the title product (b.p. 170° (air bath temperature) at 14 mmHg).

(b) N-(2-hydroxy-2-phenylethyl) N-methyl thiophene-3-ethylamine

A solution of methyl thiophene-3-ethylamine (3.3 g) and styrene oxide (1.8 ml) in acetonitrile (17 ml) was heated under reflux for 24 hours. The mixture was evaporated and the residual oil chromatographed on silica eluting with 2% methanol in dichloromethane to give the title product as an oil.

EXAMPLE 21

(a) 4-Bromo-thiophene-3-ethylamine

Bromine (18.1 ml) was added dropwise over 1 hour to a stirred solution of thiophene-3-ethylamine (12.7 g) and sodium acetate trihydrate (68 g) in acetic acid (125 ml) at room temperature. The pale suspension was heated to 50° for 16 hours to give 2,4,5-tribromo-thiophene-3-ethylamine. After allowing to cool zinc dust (16.5 g) was added portionwise over 2 hours, the mixture effervesced and became warm. Heated to reflux for 3 hours and then evaporated. Water (100 ml) was added to the residue, basified to pH~8 with 0.880 aqueous ammonia solution and extracted with dichloromethane (2×100 ml). The extracts were dried filtered, evaporated, and distilled to give the title product as a mobile liquid (b.p. 150° air bath temperature at 0.2 mmHg).

(b) N-(2-hydroxy-2-phenylethyl) 4-bromo-thiophene-3-ethylamine

N-(2-hydroxy-2-phenylethyl) 4-bromo-thiophene-3-ethylamine was prepared from 4-bromothiophene-3-ethylamine and styrene oxide by the method described in Example 1(b) and recrystallised from cyclohexane (m.p. 75°).

(c) 3-Bromo-8-phenyl-5,6,7,8-tetrahydro-4H-thieno[2,3-d]azepine hydrochloride

3-Bromo-8-phenyl-5,6,7,8-tetrahydro-4H-thieno[2,3-d]azepine hydrochloride was prepared from N-(2-hydroxy-2-phenylethyl) 4-bromo-thiophene-3-ethylamine by the method described in Example 1(c) as a white solid, m.p. 261°.

EXAMPLE 22

2-Acetyl-6-methyl-8-phenyl-5,6,7,8-tetrahydro-4H-thieno[2,3-d]azepine hydrochloride Boron trifluoride etherate (0.69 ml) was added dropwise to a stirred solution of 6-methyl-8-phenyl-5,6,7,8-tetrahydro-4H-thieno[2,3-d]azepine (0.46 g) in acetic anhydride (5 ml) at room temperature. After 16 hours, water (30 ml) and dichloromethane (30 ml) were added and the stirred mixture basified to pH~10 with 2M sodium hydroxide. This was extracted with dichloromethane (2×30 ml) and the extracts were dried, filtered and evaporated to a brown oil. Chromatography on silica eluting with 2% methanol in dichloromethane gave a yellow oil. This was dissolved in ethanol and ethanolic hydrogen chloride, evaporated and the title product recrystallised from ethanoldiethylethyl (m.p. 170°–176° C.).

EXAMPLE 23

2-Acetyl-3-bromo-6-methyl-8-phenyl-5,6,7,8-tetrahydro-4H-thieno [2,3-d]azepine hydrochloride 3-Bromo-6-methyl-8-phenyl-5,6,7,8-tetrahydro-4H-thieno[2,3-d]azepine was acetylated by the method in Example 22 to give the title product, m.p. 189° C.

EXAMPLE 24

2-Acetyl-3-chloro-6-methyl-8-phenyl-5,6,7,8-tetrahydro-4H-thieno[2,3-]azepine hydrochloride

Method 1

3-Chloro-6-methyl-8-phenyl-5,6,7,8-tetrahydro-4H-thieno[2,3-d]azepine was acetylated by the method in Example 22 to give the title product, m.p. 188° C.

Method 2

Acetyl chloride (0.14 ml) was added to a stirred mixture of 3-chloro-6-methyl-8-phenyl-5,6,7,8-tetrahydro-4H-thieno[2,3-d]azepine hydrochloride (0.31 g) and aluminium chloride (0.4 g) in 1,1,2-trichloroethane (10 ml) at room temperature. After 16 hours iced water was added, the mixture was basified with 0.880 ammonia solution and extracted with dichloromethane. The crude product was chromatographed and crystallised from ethanol and ethanolic hydrogen chloride to give the title product.

EXAMPLE 25

6-Methyl-3-methylthio-8-phenyl-5,6,7,8-tetrahydro-4H-thieno [2,3-d]azepine

3-Bromo-6-methyl-8-phenyl-5,6,7,8-tetrahydro-4H-thieno[2,3-d]azepine was reacted by the method described in Example 14 to give the title product, m.p. 93° C.

EXAMPLE 26

3,6-Dimethyl-8-phenyl-5,6,7,8-tetrahydro-4H-thieno[2,3-d]azepine

3-Bromo-6-methyl-8phenyl-5,6,7,8-tetrahydro-4H-thieno[2,3-d]azepine was reacted by the method described in Example 16 to give the title product, m.p. 40° C.

EXAMPLE 27

3-Chloro-6-methyl-8-phenyl-5,6,7,8-tetrahydro-4H-thieno[2,3-d]azepine

Anhydrous copper I chloride (0.68 g) was added to a stirred solution of 3-bromo-6-methyl-8-phenyl-5,6,7,8-tetrahydro-4H-thieno[2,3-d]azepine (1.0 g) in dry dimethylformamide under nitrogen. The mixture was heated to 120° for 5 hours, evaporated, water added and extracted with dichloromethane. The extracts were dried, filtered and evaporated and the residue chromatographed on silica, eluting with 1% methanol in dichloromethane, to give a crude product which contained 10% of the starting bromo- compound. Further purification using preparative reverse phase high pressure liquid chromatographed gave the pure title product, m.p. 67° C.

EXAMPLE 28

3-Chloro-6-methyl-8-phenyl-5,6,7,8-tetrahydro-4H-thieno[2,3-d]azepine hydrochloride

(a) 4-Bromo-thiophene-3-ethylacetamide

Acetic anhydride (72.5 ml) was added to a stirred solution of thiophene-3-ethylamine (65 g) in acetic acid (500 ml) at room temperature under nitrogen. After 15 minutes a solution of sodium hydroxide (100 g) in water (100 ml) was added dropwise. The mixture became warm. Bromine (270 g) was added dropwise over 1 hour and the mixture heated under reflux for 7 hours. Extra bromine (90 g) was added and the mixture heated for a further 1½ hours.

Zinc powder (98 g) was added portionwise to the stirred mixture (caution: vigorous foaming occurred) and heated for 17 hours, then extra zinc powder (33 g) was added portionwise and the mixture heated under reflux for 5 hours. After allowing to cool the viscous mixture was poured onto water (1.5 L) and 2M hydrochloric acid (250 ml) and extracted with dichloromethane (2×750 ml). The extracts were washed with 2M hydrochloric acid (2×500 ml), aqueous ammonia (2×500 ml), water (2×500 ml), dried, filtered and evaporated to a brown oil of 4-bromo-thiophene-3-ethylacetamide.

(b) N-Methyl 4-bromo-thiophene-3-ethylacetamide

A solution of 4-bromo-thiophene-3-ethyl-acetamide (71.3 g) in dry dimethylformamide (72 ml) was added dropwise to a stirred suspension of sodium hydride (50% dispersion in oil 14.4 g) in dry dimethylformamide (200 ml) at 50° under nitrogen. When effervescence had stopped (3 hours) the mixture was cooled to 5°–10° and a solution of methyl iodide (19 ml) in dry dimethylformamide (70 ml) was added dropwise. After 2 hours ethanol (20 ml) was added to destroy any sodium hydride remaining and the mixture evaporated. Water (500 ml) was added to the residue and then extracted with dichloromethane (2×500 ml). The extracts were dried, filtered and evaporated to give an oil of the N-methylated product.

(c) N-methyl 4-chloro-thiophene-3-ethylacetamide

A mixture of anhydrous copper (I) chloride (45.3 g) and N-methyl 4-bromo-thiophene-3-ethylacetamide (40 g) in dry dimethylformamide (200 ml) was heated to 130° for 8 hours under nitrogen. The mixture was evaporated, 2M hydrochloric acid (400 ml) added to the residue and extracted with dichloromethane (2×200 ml). The extracts were dried, filtered and evaporated to a brown oil of the chloro- product.

(d) N-Methyl 4-Chloro-thiophene-3-ethylamine

A solution of N-methyl 4-chloro-thiophene-3-ethylacetamide (35 g) and 50% aqueous sodium hydroxide (55 ml) in ethanol (150 ml) was heated under reflux for 22 hours. It was evaporated. Water (100 ml) was added to the residue and then extracted with dichloromethane (2×125 ml). The dichloromethane extracts were extracted with 2M hydrochloric acid (2×100 ml). The aqueous acid solution was basified with 0.880 ammonia solution to pH~10 and extracted with dichloromethane (2×100 ml). The extracts were dried, filtered and evaporated to a brown oil. Distillation gave a colourless mobile oil of N-methyl 4-chlorothiophene-3-ethylamine (b.p. 98°–102° C./10 mmHg).

(e) N-(2-Hydroxy-2-phenylethyl)N-methyl 4-chloro-thiophene-3-ethylamine

N-methyl 4-chloro-thiophene-3-ethylamine was reacted with styrene oxide as described in Example 20(b) to give the title product as an oil.

(f) 3-Chloro-6-methyl-8-phenyl-5,6,7,8-tetrahydro-4H-thieno[2,3-d]azepine hydrochloride N-(2-Hydroxy-2-phenylethyl) N-methyl 4-chlorothiophene-3-ethylamine was cyclised as described in Example 1(c) to give the title product.

EXAMPLE 29

3-Chloro-6-methyl-8-phenyl-5,6,7,8-tetrahydro-4H-thieno[2,3-d]azepine-2-carboxaldehyde hydrochloride 3-Chloro-6-methyl-8-phenyl-5,6,7,8-tetrahydro-4H-thieno[2,3-d]azepine hydrochloride was formylated by the method described in Example 7 to give 3-chloro-6-methyl-8-phenyl-5,6,7,8-tetrahydro-4H-thieno[2,3-d]-azepine-2-carboxaldehyde as an oil. Conversion to the hydrochloride salt gave the title product, m.p. 197° C.

EXAMPLE 30

3-Chloro-2-hydroxymethyl-6-methyl-8-phenyl-5,6,7,8-tetrahydro-4H-thieno[2,3d]azepine 3-Chloro-6-methyl-8-phenyl-5,6,7,8-tetrahydro-4H-thieno[2,3-d]azepine-2-carboxaldehyde was reduced by the method described in Example 8 to give a white solid of the title product, m.p. 139° C.

EXAMPLE 31

3-Chloro-2,6-dimethyl-8-phenyl-5,6,7,8-tetrahydro-4H-thieno[2,3-d]azepine hydrochloride A mixture of 3-chloro-2-hydroxymethyl-6-methyl-8-phenyl-5,6,7,8-tetrahydro-4H-thieno[2,3-d]azepine (0.20 g) and 10% palladium on carbon (50 mg) in acetic acid (2 ml) and concentrated hydrochloric acid (0.1 ml) was hydrogenated at 60 psi for 20 hours. The reaction mixture was filtered, evaporated and the residue chromatographed on silica eluting with 1% methanol-ammonia solution in dichloromethane. The combined fractions were dissolved in ethanolic hydrogen chloride, evaporated and crystallised from ethanol-diethylether to give the title product, m.p. 146° C.

EXAMPLE 32

2,3-Dichloro-6-methyl-8-phenyl-5,6,7,8-tetrahydro-4H-thieno[2,3-d]azepine hydrochloride 3-Chloro-6-methyl-8-phenyl-5,6,7,8-tetrahydro-4H-thieno[2,3-d]azepine was chlorinated by the method described in Example 12 to give the title product, m.p. 174°.

EXAMPLE 33

2-Bromo-3-chloro-6-methyl-8-phenyl-5,6,7,8-tetrahydro-4H-thieno[2,3-d]azepine hydrochloride 3-Chloro-6-methyl-8-phenyl-5,6,7,8-tetrahydro-4H-thieno[2,3-d]azepine was brominated by the method described in Example 9 to give the title product, m.p. 200° C.

EXAMPLE 34 rel-(R,R)- and rel(R,S)-3-Chloro-2-(1-hydroxyethyl)-6-methyl-8-phenyl-5,6,7,8-tetrahydro-4H-thieno[2,3-d]azepine 2-Acetyl-3-chloro-6-methyl-8-phenyl-5,6,7,8-tetrahydro-4H-thieno[2,3-d]azepine was reduced by the method described in Example 8 to give a 1:1 mixture of the title products. Fractional crystallisation from cyclohexane gave one of the title products, m.p. 113°. Evaporation of the mother liquors and recrystallisation from cyclohexane gave the other title product, m.p. 127° C.

EXAMPLE 35

2-(3-Chloro-6-methyl-8phenyl-5,6,7,8-tetrahydro[2,3-d]azepine-2-yl)propan-2-ol

A solution of methylmagnesium chloride (0.63 ml, 1.9 mmol, 3M in tetrahydrofuran) was added dropwise to a stirred solution of 2-acetyl-3-chloro-6-methyl-8-phenyl-5,6,7,8-tetrahydro[2,3-d]azepine (0.20 g) in dry tetrahydrofuran (20 ml) at room temperature under nitrogen. After 20 hours water was added and the mixture extracted with dichloromethane. The extracts were dried filtered and evaporated to a pale yellow solid which was recrystallised from cyclohexane to give the title product, m.p. 178° C.

EXAMPLE 36

6-Methyl-8-phenyl-5,6,7,8-tetrahydro-4H-thieno[2,3-d]azepine-3-carbonitrile

(a) 3-Bromo-8-phenyl-5,6,7,8-tetrahydro-6-trifluoroacetyl-4H-thieno[2,3-d]azepine Trifluoroacetic anhydride (0.55 ml) was added dropwise to a stirred solution of 3-bromo-8-phenyl-5,6,7,8-tetrahydro-4H-thieno[2,3-d]azepine hydrochloride (0.90 g) and triethylamine (0.90 ml) in dichloromethane (20 ml) at room temperature under nitrogen. After 15 minutes water was added and the dichloromethane solution was washed with water (2×10 ml), dried, filtered and evaporated to give the trifluoroacylated product, m.p. 115°.

(b) 8-Phenyl-5,6,7,8-tetrahydro-6-trifluoroacetyl-4H-thieno-[2,3-d]-azepine-3-carbonitrile A mixture of copper (I) cyanide (0.45 g) and 3-bromo-8-phenyl-5,6,7,8-tetrahydro-6-trifluoroacetyl-4H-thieno[2,3-d]azepine (1.0 g) in dry dimethylformamide (10 ml) was heated under reflux for 5 hours. After allowing to cool to room temperature methanol (35 ml) was added and the mixture stirred vigorously, filtered and the filtrate evaporated to a yellow oil. Chromatography on silica eluting with diethylether gave the nitrile product, m.p. 107°.

(c)

8-Phenyl-5,6,7,8-tetrahydro-4H-thieno[2,3-d]azepine-3-carbonitrile hydrochloride A solution of methanol-ammonia (5M, 4 ml) was added to a stirred suspension of 8-phenyl-5,6,7,8-tetrahydro-6-trifluoroacetyl-4H-thieno[2,3-d]azepine-3-carbonitrile (0.75 g) in methanol (10 ml). After 5 hours at room temperature the clear solution was evaporated, the residual oil dissolved in ethanol and ethanolic hydrogen chloride, and evaporated. The residual solid was recrystallised from ethanol to give 8-phenyl-5,6,7,8-tetrahydro-4H-thieno[2,3-d]azepine-3-carbonitrile hydrochloride, m.p. 261°.

(d)

6-Methyl-8-phenyl-5,6,7,8-tetrahydro-4H-thieno[2,3-d]azepine-3-carbonitrile hydrochloride 8-Phenyl-5,6,7,8-tetrahydro-4H-thieno[2,3-d]azepine-3-carbonitrile hydrochloride (0.40 g) was reacted as described in Example 2, method 1 to give the title product, m.p. 224°.

EXAMPLE 37

6-Methyl-8-phenyl-5,6,7,8-tetrahydro-4H-thieno[2,3-d]azepine-3-carboxaldehyde

6Methyl-8-phenyl-5,6,7,8-tetrahydro-4H-thieno[2,3-d]azepine-3-carbonitrile hydrochloride (0.25 g) was converted to the free base by extraction between dichloromethane and aqueous ammonia. A suspension of lithium triethoxyaluminohydride (1.3M in diethylether, 1.4 ml) was added to a stirred suspension of the dried free base in diethylether (5 ml) cooled in an ice bath. After 1 hour at room temperature, water (1 ml) and 2M hydrochloric acid (3 ml) was added and the mixture stirred vigorously. The mixture was basified with 0.880 ammonia solution and extracted with diethylether. The extracted product was chromatographed on silica to give the title product, m.p. 77°.

EXAMPLE 38

3-Hydroxymethyl-6-methyl-8-phenyl-5,6,7,8-tetrahydro-4H-thieno[2,3-d]azepine

6-Methyl-8-phenyl-5,6,7,8-tetrahydro-4H-thieno[2,3-d]azepine-3-carboxaldehyde was reduced by the method described in Example 8 to give the title product, m.p. 115°.

EXAMPLE 39

2-Hydroxymethyl-6-methyl-3-methylthio-8-phenyl-5,6,7,8-tetrahydro-4H-thieno[2,3-d]azepine 6-Methyl-3-methylthio-8-phenyl-5,6,7,8-tetrahydro-4H-thieno[2,3-d]azepine was formylated by the method described in Example 7 to give 6-methyl-3-methylthio-8-phenyl-5,6,7,8-tetrahydro-4H-thieno[2,3-d]azepine-2-carboxaldehyde which was then reduced as in Example 8 to give the title product, m.p. 146°.

EXAMPLE 40

8-(7-Benzofuranyl)-3-bromo-6-methyl-5,6,7,8-tetrahydro-4H-thieno[2,3-d]azepine hydrochloride (a) A solution of benzofuran-7-carboxaldehyde (4.4 g) in dry dimethylsulphoxide was added dropwise to a stirred solution of sodium hydride (60% dispersion in oil, 2.5 g) and trimethylsulphoxonium iodide (7.6 g) in dimethylsulphoxide (50 ml) at room temperature. After 1 hour iced water was added and extracted with diethylether. The extracts were washed with water, dried, filtered and evaporated to a yellow oil. Chromatography on silica eluting with 10:1:90 ether:triethylamine:hexane gave 7-benzofuranyl oxirane as an oil.

(b) N-Methyl 4-bromo-thiophene-3-ethylamine was reacted with 7-benzofuranyl oxirane as in Example 1(b) and the product cyclised as in Example 1(c) to give the title product, m.p. 222°.

The following Examples illustrate the preparation of typical formulations containing an active ingredient according to the invention.

EXAMPLE 41

Hard gelatin capsule

Each capsule contains

| Active ingredient | 10 mg |
|---|---|
| 1% Silicone starch | 250 mg |

The active ingredient is blended with the 1% silicone starch and the formulation is filled into gelatin capsules.

EXAMPLE 42

Tablet

Each tablet contains

| Active ingredient | 10 mg |
|---|---|
| Calcium carbonate | 300 mg |
| Magnesium stearate | 10 mg |
| Starch | 30 mg |
| Hydroxypropylmethyl cellulose | 10 mg |
| Iron oxide | 4 mg |

The active ingredient is granulated with calcium carbonate and starch. The dried granulate is blended with lubricant and disintegrant and compressed into tablets of the required dosage strength. The tablet may then be coated.

EXAMPLE 43

Injection

| Active ingredient | 10 mg |
|---|---|
| Water | 1 mg |

The active ingredient is dissolved in water and distributed into vials, ampoules or pre-pack syringes using appropriate equipment. The product is sterilised.

We claim:

1. A compound of the formula

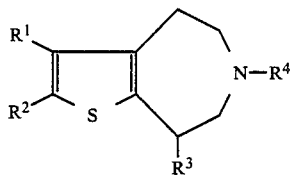

in which:
- $R^1$ is hydrogen, hydroxy, nitro, cyano, halo, amino, acetamido, hydroxy-$C_{1-4}$ alkyl, carboxaldehydo, $C_{1-4}$ alkyl-carbonyl, carboxy, $C_{1-4}$ alkoxy-carbonyl, $C_{1-4}$ alkyl, $C_{1-4}$ alkoxy, $C_{1-4}$ alkylthio, $C_{1-4}$ alkylsulphonyl or $C_{1-4}$ alkoxy-$C_{1-4}$ alkyl;
- $R^2$ is hydrogen, hydroxy, nitro, cyano, halo, amino, carboxamido, acetamido, hydroxy-$C_{1-4}$ alkyl, carboxaldehydo, $C_{1-4}$ alkylcarbonyl, carboxy, $C_{1-4}$ alkoxycarbonyl, $C_{1-4}$ alkyl, $C_{1-4}$ alkoxy, $C_{1-4}$ alkylthio, $C_{1-4}$ alkylsulphonyl, $C_{1-4}$ alkoxy-$C_{1-4}$ alkyl, oximino or aminomethyl;
- $R^3$ is naphthyl, benzofuranyl, dihydrobenzofuranyl, benzothienyl, chromanyl, chromenyl, indolyl, indolinyl, indanyl, indenyl, 1,2,3,4-tetrahydronaphthyl, dihydronaphthyl, or quinolinyl, each of which may be substituted with halogen, hydroxy, or $C_{1-4}$ alkoxy;
- or $R^3$ is phenyl optionally substituted with one or more substituents selected from the group consisting of nitro, cyano, amino, hydroxyl, trifluoromethyl, $C_{1-4}$ alkyl, $C_{1-4}$ alkoxy, and halo;
- $R^4$ is hydrogen, $C_{1-4}$ alkyl, or $C_{2-4}$ alkenyl;
- or $R^4$ is benzyl optionally substituted on the phenyl nucleus with one or more substituents selected from the group consisting of nitro, cyano, amino, hydroxyl, trifluoromethyl, $C_{1-4}$ alkyl, $C_{1-4}$ alkoxy, and halogen;
or a salt thereof.

2. A compound according to claim 1 in which $R^3$ is phenyl or benzofuranyl.

3. A compound according to either of claims 1 and 2 in which $R^1$ is hydrogen, halo or $C_{1-4}$ alkylthio, and $R^2$ is hydrogen, hydroxy-$C_{1-4}$ alkyl, halo or $C_{1-4}$ alkyl.

4. A compound according to claim 3 in which $R^4$ is $C_{1-4}$ alkyl.

5. A compound of formula

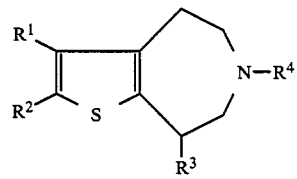

in which $R^1$ is halogen or $C_{1-4}$ alkylthio, $R^2$ is hydrogen, hydroxy-$C_{1-4}$ alkyl, $C_{1-4}$ alkyl or halo, $R^3$ is phenyl or benzofuranyl, and $R^4$ is hydrogen or $C_{1-4}$ alkyl, or a salt thereof.

6. A compound of formula

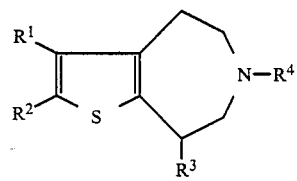

in which $R^1$ is hydrogen, halo or $C_{1-4}$ alkylthio, $R^2$ is hydrogen, hydroxymethyl, halo or $C_{1-4}$ alkyl, $R^3$ is phenyl or benzofuranyl and $R^4$ is hydrogen or $C_{1-4}$ alkyl, or a salt thereof.

7. A pharmaceutical formulation which comprises a compound according to claim 1 or a pharmaceutically-acceptable salt thereof, in association with a pharmaceutically-acceptable diluent or carrier therefor.

8. A method of treating a mammal, including a human, suffering from or susceptible to a disease of the central nervous system which comprises administering an effective amount of a compound as defined in claim 1, or a pharmaceutically-acceptable salt thereof.

* * * * *